(12) United States Patent
Prus et al.

(10) Patent No.: US 8,617,073 B2
(45) Date of Patent: Dec. 31, 2013

(54) FOCUSING ULTRASOUND INTO THE BRAIN THROUGH THE SKULL BY UTILIZING BOTH LONGITUDINAL AND SHEAR WAVES

(75) Inventors: Oleg Prus, Haifa (IL); Shuki Vitek, Haifa (IL)

(73) Assignee: Insightec Ltd., Tirat Carmel (IL)

( * ) Notice: Subject to any disclaimer, the term of this patent is extended or adjusted under 35 U.S.C. 154(b) by 840 days.

(21) Appl. No.: 12/425,698

(22) Filed: Apr. 17, 2009

(65) Prior Publication Data

US 2010/0268088 A1    Oct. 21, 2010

(51) Int. Cl.
A61B 8/00    (2006.01)

(52) U.S. Cl.
USPC ............ 600/437; 600/407; 600/442; 600/448

(58) Field of Classification Search
USPC .......... 310/328; 600/437–439, 441–443, 447, 600/449, 458, 459; 601/2, 3; 604/22; 73/620
See application file for complete search history.

(56) References Cited

U.S. PATENT DOCUMENTS

| | | |
|---|---|---|
| 2,795,709 A | 6/1957 | Camp |
| 3,142,035 A | 7/1964 | Harris |
| 3,942,150 A | 3/1976 | Booth et al. |
| 3,974,475 A | 8/1976 | Burckhardt et al. |
| 3,992,693 A | 11/1976 | Martin et al. |
| 4,000,493 A | 12/1976 | Spaulding et al. |
| 4,074,564 A | 2/1978 | Anderson |
| 4,206,653 A | 6/1980 | Lemay |
| 4,221,132 A * | 9/1980 | Poole ............................. 73/620 |
| 4,307,613 A | 12/1981 | Fox |
| 4,339,952 A | 7/1982 | Foster |
| 4,454,597 A | 6/1984 | Sullivan |
| 4,478,083 A | 10/1984 | Hassler et al. |
| 4,505,156 A | 3/1985 | Questo |
| 4,526,168 A | 7/1985 | Hassler et al. |
| 4,537,074 A | 8/1985 | Dietz |
| 4,549,533 A | 10/1985 | Cain et al. |
| 4,554,925 A | 11/1985 | Young |
| 4,662,222 A | 5/1987 | Johnson |
| 4,817,614 A * | 4/1989 | Hassler et al. ................ 600/441 |
| 4,858,597 A | 8/1989 | Kurtze et al. |
| 4,865,042 A | 9/1989 | Umemura et al. |
| 4,888,746 A | 12/1989 | Wurster et al. |
| 4,889,122 A | 12/1989 | Watmough et al. |

(Continued)

FOREIGN PATENT DOCUMENTS

| | | |
|---|---|---|
| DE | 4345308 C2 | 2/2001 |
| EP | 1132054 | 9/2001 |

(Continued)

OTHER PUBLICATIONS

Clement et al., "A non-invasive method for focusing ultrasound through the human skull", Phys. Med. Biol. 47 (2002) pp. 1219-1236.*

(Continued)

Primary Examiner — Unsu Jung
Assistant Examiner — Serkan Akar
(74) Attorney, Agent, or Firm — Bingham McCutchen LLP

(57) ABSTRACT

Systems and methods for focusing ultrasound through the skull into the brain for diagnostic or therapeutic purposes may be improved by utilizing both longitudinal and shear waves. The relative contribution of the two modes may be determined based on the angle of incidence.

23 Claims, 8 Drawing Sheets

(56) References Cited

U.S. PATENT DOCUMENTS

| | | | | |
|---|---|---|---|---|
| 4,893,284 A | | 1/1990 | Magrane | |
| 4,893,624 A | | 1/1990 | Lele | |
| 4,937,767 A | | 6/1990 | Reuschel et al. | |
| 5,197,475 A | * | 3/1993 | Antich et al. | 600/437 |
| 5,209,221 A | | 5/1993 | Riedlinger | |
| 5,211,160 A | | 5/1993 | Talish et al. | |
| 5,247,935 A | | 9/1993 | Cline et al. | |
| 5,271,400 A | | 12/1993 | Dumoulin et al. | |
| 5,275,165 A | | 1/1994 | Ettinger et al. | |
| 5,291,890 A | | 3/1994 | Cline et al. | |
| 5,307,812 A | | 5/1994 | Hardy et al. | |
| 5,307,816 A | | 5/1994 | Hashimoto et al. | |
| 5,318,025 A | | 6/1994 | Dumoulin et al. | |
| 5,323,779 A | | 6/1994 | Hardy et al. | |
| 5,327,884 A | | 7/1994 | Hardy et al. | |
| 5,329,930 A | | 7/1994 | Thomas, III et al. | |
| 5,368,031 A | | 11/1994 | Cline et al. | |
| 5,368,032 A | | 11/1994 | Cline et al. | |
| 5,379,642 A | | 1/1995 | Reckwerdt et al. | |
| 5,391,140 A | | 2/1995 | Schaetzle et al. | |
| 5,413,550 A | | 5/1995 | Castel | |
| 5,435,312 A | | 7/1995 | Spivey et al. | |
| 5,443,068 A | | 8/1995 | Cline et al. | |
| 5,474,071 A | | 12/1995 | Chapelon et al. | |
| 5,485,839 A | | 1/1996 | Aida et al. | |
| 5,490,840 A | | 2/1996 | Uzgiris et al. | |
| 5,507,790 A | | 4/1996 | Weiss | |
| 5,520,188 A | | 5/1996 | Hennige et al. | |
| 5,520,612 A | * | 5/1996 | Winder et al. | 601/2 |
| 5,526,814 A | | 6/1996 | Cline et al. | |
| 5,549,638 A | | 8/1996 | Burdette | |
| 5,553,618 A | | 9/1996 | Suzuki et al. | |
| 5,573,497 A | | 11/1996 | Chapelon | |
| 5,582,578 A | | 12/1996 | Zhong et al. | |
| 5,590,653 A | | 1/1997 | Aida et al. | |
| 5,590,657 A | | 1/1997 | Cain et al. | |
| 5,601,526 A | | 2/1997 | Chapelon et al. | |
| 5,605,154 A | | 2/1997 | Ries et al. | |
| 5,606,971 A | * | 3/1997 | Sarvazyan | 600/438 |
| 5,617,371 A | | 4/1997 | Williams | |
| 5,617,857 A | | 4/1997 | Chader et al. | |
| 5,643,179 A | | 7/1997 | Fujimoto | |
| 5,662,170 A | | 9/1997 | Donovan et al. | |
| 5,665,054 A | | 9/1997 | Dory | |
| 5,666,954 A | | 9/1997 | Chapelon et al. | |
| 5,676,673 A | | 10/1997 | Ferre et al. | |
| 5,687,729 A | | 11/1997 | Schaetzle | |
| 5,694,936 A | | 12/1997 | Fujimoto et al. | |
| 5,711,300 A | | 1/1998 | Schneider et al. | |
| 5,722,411 A | | 3/1998 | Suzuki et al. | |
| 5,728,062 A | * | 3/1998 | Brisken | 604/22 |
| 5,739,625 A | | 4/1998 | Falcus | |
| 5,743,863 A | | 4/1998 | Chapelon | |
| 5,752,515 A | * | 5/1998 | Jolesz et al. | 600/458 |
| 5,759,162 A | | 6/1998 | Oppelt et al. | |
| 5,762,616 A | | 6/1998 | Talish | |
| 5,769,790 A | | 6/1998 | Watkins et al. | |
| 5,810,008 A | | 9/1998 | Dekel et al. | |
| 5,810,731 A | * | 9/1998 | Sarvazyan et al. | 600/438 |
| 5,873,845 A | | 2/1999 | Cline et al. | |
| 5,897,495 A | | 4/1999 | Aida et al. | |
| 5,904,659 A | * | 5/1999 | Duarte et al. | 601/2 |
| 5,938,600 A | | 8/1999 | Van Vaals et al. | |
| 5,938,608 A | | 8/1999 | Bieger et al. | |
| 5,947,900 A | | 9/1999 | Derbyshire et al. | |
| 5,984,881 A | | 11/1999 | Ishibashi et al. | |
| 6,004,269 A | | 12/1999 | Crowley et al. | |
| 6,023,636 A | | 2/2000 | Wendt et al. | |
| 6,042,556 A | | 3/2000 | Beach et al. | |
| 6,071,239 A | | 6/2000 | Cribbs et al. | |
| 6,113,559 A | | 9/2000 | Klopotek | |
| 6,128,522 A | | 10/2000 | Acker et al. | |
| 6,128,958 A | | 10/2000 | Cain | |
| 6,135,960 A | * | 10/2000 | Holmberg | 600/447 |
| 6,193,659 B1 | | 2/2001 | Ramamurthy et al. | |
| 6,217,530 B1 | * | 4/2001 | Martin et al. | 601/2 |
| 6,242,915 B1 | | 6/2001 | Hurd | |
| 6,246,896 B1 | | 6/2001 | Dumoulin et al. | |
| 6,263,230 B1 | | 7/2001 | Haynor et al. | |
| 6,267,734 B1 | | 7/2001 | Ishibashi et al. | |
| 6,289,233 B1 | | 9/2001 | Dumoulin et al. | |
| 6,309,355 B1 | | 10/2001 | Cain et al. | |
| 6,317,619 B1 | | 11/2001 | Boernert et al. | |
| 6,322,527 B1 | | 11/2001 | Talish | |
| 6,334,846 B1 | | 1/2002 | Ishibashi et al. | |
| 6,374,132 B1 | | 4/2002 | Acker et al. | |
| 6,392,330 B1 | | 5/2002 | Zloter et al. | |
| 6,397,094 B1 | | 5/2002 | Ludeke et al. | |
| 6,413,216 B1 | | 7/2002 | Cain et al. | |
| 6,419,648 B1 | | 7/2002 | Vitek et al. | |
| 6,424,597 B1 | | 7/2002 | Bolomey et al. | |
| 6,425,867 B1 | | 7/2002 | Vaezy et al. | |
| 6,428,532 B1 | | 8/2002 | Doukas et al. | |
| 6,433,464 B2 | * | 8/2002 | Jones | 310/328 |
| 6,461,314 B1 | | 10/2002 | Pant et al. | |
| 6,475,150 B2 | | 11/2002 | Haddad | |
| 6,478,739 B1 | | 11/2002 | Hong | |
| 6,506,154 B1 | | 1/2003 | Ezion et al. | |
| 6,506,171 B1 | | 1/2003 | Vitek et al. | |
| 6,511,064 B1 | * | 1/2003 | Phinney et al. | 271/262 |
| 6,511,428 B1 | | 1/2003 | Azuma et al. | |
| 6,522,142 B1 | | 2/2003 | Freundlich | |
| 6,523,272 B1 | | 2/2003 | Morales | |
| 6,524,251 B2 | * | 2/2003 | Rabiner et al. | 600/439 |
| 6,559,644 B2 | | 5/2003 | Froundlich et al. | |
| 6,566,878 B1 | | 5/2003 | Komura et al. | |
| 6,582,381 B1 | | 6/2003 | Yehezkeli et al. | |
| 6,599,256 B1 | | 7/2003 | Acker et al. | |
| 6,612,988 B2 | | 9/2003 | Maor et al. | |
| 6,613,004 B1 | | 9/2003 | Vitek et al. | |
| 6,613,005 B1 | | 9/2003 | Friedman et al. | |
| 6,618,608 B1 | | 9/2003 | Watkins et al. | |
| 6,618,620 B1 | | 9/2003 | Freundlich et al. | |
| 6,626,854 B2 | | 9/2003 | Friedman et al. | |
| 6,626,855 B1 | | 9/2003 | Weng et al. | |
| 6,629,929 B1 | | 10/2003 | Jago et al. | |
| 6,645,162 B2 | | 11/2003 | Friedman et al. | |
| 6,652,461 B1 | | 11/2003 | Levkovitz | |
| 6,666,833 B1 | | 12/2003 | Friedman et al. | |
| 6,676,601 B1 | | 1/2004 | Lacoste et al. | |
| 6,679,855 B2 | | 1/2004 | Horn et al. | |
| 6,705,994 B2 | | 3/2004 | Vortman et al. | |
| 6,719,694 B2 | | 4/2004 | Weng et al. | |
| 6,733,450 B1 | | 5/2004 | Alexandrov et al. | |
| 6,735,461 B2 | | 5/2004 | Vitek et al. | |
| 6,761,691 B2 | | 7/2004 | Tsuzuki | |
| 6,770,031 B2 | | 8/2004 | Hynynen et al. | |
| 6,770,039 B2 | | 8/2004 | Zhong et al. | |
| 6,788,619 B2 | | 9/2004 | Calvert | |
| 6,790,180 B2 | | 9/2004 | Vitek | |
| 6,824,516 B2 | | 11/2004 | Batten et al. | |
| 6,951,540 B2 | | 10/2005 | Ebbini et al. | |
| 6,961,606 B2 | | 11/2005 | DeSilets et al. | |
| 7,001,379 B2 | | 2/2006 | Behl et al. | |
| 7,077,820 B1 | | 7/2006 | Kadziauskas et al. | |
| 7,094,205 B2 | | 8/2006 | Marmarelis | |
| 7,128,711 B2 | | 10/2006 | Medan et al. | |
| 7,155,271 B2 | | 12/2006 | Halperin et al. | |
| 7,175,596 B2 | | 2/2007 | Vitek et al. | |
| 7,175,599 B2 | * | 2/2007 | Hynynen et al. | 600/443 |
| 7,264,592 B2 | | 9/2007 | Shehada | |
| 7,264,597 B2 | | 9/2007 | Cathignol | |
| 7,267,650 B2 | | 9/2007 | Chow et al. | |
| 7,344,509 B2 | | 3/2008 | Hynynen et al. | |
| 7,377,900 B2 | | 5/2008 | Vitek et al. | |
| 7,429,248 B1 | * | 9/2008 | Winder et al. | 601/2 |
| 7,452,357 B2 | | 11/2008 | Vlegele et al. | |
| 7,505,805 B2 | | 3/2009 | Kuroda | |
| 7,505,808 B2 | | 3/2009 | Anderson et al. | |
| 7,507,213 B2 | * | 3/2009 | Schultheiss et al. | 601/2 |
| 7,510,536 B2 | | 3/2009 | Foley et al. | |
| 7,511,501 B2 | | 3/2009 | Wexler | |
| 7,535,794 B2 | | 5/2009 | Prus et al. | |
| 7,553,284 B2 | | 6/2009 | Vaitekunas | |

(56) References Cited

U.S. PATENT DOCUMENTS

| | | | |
|---|---|---|---|
| 7,603,162 B2 | 10/2009 | Danz et al. | |
| 7,611,462 B2 | 11/2009 | Vortman et al. | |
| 7,652,410 B2 | 1/2010 | Prus | |
| 7,699,780 B2 | 4/2010 | Vitek et al. | |
| 2001/0031922 A1 | 10/2001 | Weng et al. | |
| 2002/0016557 A1* | 2/2002 | Duarte et al. | 601/2 |
| 2002/0035779 A1 | 3/2002 | Krieg et al. | |
| 2002/0082589 A1 | 6/2002 | Friedman et al. | |
| 2002/0095087 A1* | 7/2002 | Mourad et al. | 600/442 |
| 2002/0161300 A1* | 10/2002 | Hoff et al. | 600/449 |
| 2002/0188229 A1 | 12/2002 | Ryaby | |
| 2003/0004439 A1 | 1/2003 | Pant et al. | |
| 2003/0060820 A1 | 3/2003 | Maguire et al. | |
| 2003/0187371 A1 | 10/2003 | Vortman et al. | |
| 2004/0030251 A1 | 2/2004 | Ebbini et al. | |
| 2004/0068186 A1 | 4/2004 | Ishida et al. | |
| 2004/0122316 A1 | 6/2004 | Satoh | |
| 2004/0122323 A1 | 6/2004 | Vortman et al. | |
| 2004/0143187 A1* | 7/2004 | Biagi et al. | 600/437 |
| 2004/0210134 A1* | 10/2004 | Hynynen et al. | 600/439 |
| 2004/0210135 A1* | 10/2004 | Hynynen et al. | 600/439 |
| 2004/0236253 A1 | 11/2004 | Vortman et al. | |
| 2004/0267126 A1 | 12/2004 | Takeuchi | |
| 2005/0033201 A1 | 2/2005 | Takahashi et al. | |
| 2005/0096542 A1 | 5/2005 | Weng et al. | |
| 2005/0131301 A1 | 6/2005 | Peszynski et al. | |
| 2005/0203444 A1 | 9/2005 | Schonenberger et al. | |
| 2005/0251046 A1 | 11/2005 | Yamamoto et al. | |
| 2006/0052661 A1 | 3/2006 | Gannot et al. | |
| 2006/0052701 A1 | 3/2006 | Carter et al. | |
| 2006/0058678 A1 | 3/2006 | Vitek et al. | |
| 2006/0106300 A1 | 5/2006 | Seppenwoolde et al. | |
| 2006/0173385 A1 | 8/2006 | Lidgren et al. | |
| 2006/0184034 A1* | 8/2006 | Haim et al. | 600/459 |
| 2006/0184069 A1* | 8/2006 | Vaitekunas | 601/2 |
| 2006/0206105 A1 | 9/2006 | Chopra et al. | |
| 2006/0229594 A1 | 10/2006 | Francischelli et al. | |
| 2007/0016039 A1 | 1/2007 | Vortman et al. | |
| 2007/0055140 A1 | 3/2007 | Kuroda | |
| 2007/0066897 A1 | 3/2007 | Sekins et al. | |
| 2007/0073135 A1 | 3/2007 | Lee et al. | |
| 2007/0098232 A1 | 5/2007 | Matula et al. | |
| 2007/0167781 A1 | 7/2007 | Vortman et al. | |
| 2007/0197918 A1 | 8/2007 | Vitek et al. | |
| 2007/0219470 A1 | 9/2007 | Talish et al. | |
| 2007/0276237 A1 | 11/2007 | Li | |
| 2008/0027342 A1 | 1/2008 | Rouw et al. | |
| 2008/0031090 A1* | 2/2008 | Prus et al. | 367/13 |
| 2008/0033278 A1 | 2/2008 | Assif | |
| 2008/0082026 A1 | 4/2008 | Schmidt et al. | |
| 2008/0108900 A1 | 5/2008 | Lee et al. | |
| 2008/0183077 A1 | 7/2008 | Moreau-Gobard et al. | |
| 2008/0228081 A1 | 9/2008 | Becker et al. | |
| 2008/0312562 A1 | 12/2008 | Routh et al. | |
| 2009/0088623 A1 | 4/2009 | Vortman et al. | |
| 2009/0118619 A1 | 5/2009 | Oshiki | |
| 2010/0030076 A1 | 2/2010 | Vortman et al. | |
| 2010/0056962 A1 | 3/2010 | Vortman et al. | |
| 2010/0125193 A1 | 5/2010 | Zadicario | |
| 2010/0179425 A1 | 7/2010 | Zadicario | |
| 2010/0268088 A1* | 10/2010 | Prus et al. | 600/459 |
| 2010/0318002 A1 | 12/2010 | Prus et al. | |

FOREIGN PATENT DOCUMENTS

| | | |
|---|---|---|
| EP | 1591073 | 11/2005 |
| EP | 1774920 A1 | 4/2007 |
| EP | 1790384 | 5/2007 |
| EP | 1936404 | 6/2008 |
| FR | 2806611 A1 | 9/2001 |
| JP | 5-92008 | 4/1993 |
| JP | 7-184907 | 7/1995 |
| JP | 7-231895 | 9/1995 |
| JP | 7-313518 | 12/1995 |
| JP | 11313833 A | 11/1999 |
| JP | 00/166940 | 6/2000 |
| JP | 01/516075 | 9/2001 |
| JP | 02/530145 | 9/2002 |
| WO | WO-9100059 A1 | 1/1991 |
| WO | WO-9852465 A1 | 11/1998 |
| WO | WO-00/031614 | 6/2000 |
| WO | WO-0031614 A1 | 6/2000 |
| WO | WO-0166189 A1 | 9/2001 |
| WO | WO-01/080709 | 11/2001 |
| WO | WO-0180709 A2 | 11/2001 |
| WO | WO-02/43805 | 6/2002 |
| WO | WO-02058791 A1 | 8/2002 |
| WO | WO-03/013654 | 2/2003 |
| WO | WO-03/013654 A1 | 2/2003 |
| WO | WO-03097162 A2 | 11/2003 |
| WO | WO-03098232 A2 | 11/2003 |
| WO | WO-2004/093686 | 11/2004 |
| WO | WO-200558029 A2 | 6/2005 |
| WO | WO-2006/018837 | 2/2006 |
| WO | WO-2006018837 A2 | 2/2006 |
| WO | WO-2006025001 A1 | 3/2006 |
| WO | WO-2006087649 A1 | 8/2006 |
| WO | WO-2006/119572 | 11/2006 |
| WO | WO-2007073551 A1 | 6/2007 |
| WO | WO-2008/039449 | 4/2008 |
| WO | WO-2008050278 A1 | 5/2008 |
| WO | WO-200875203 A2 | 6/2008 |
| WO | WO-2008119054 A1 | 10/2008 |
| WO | WO-2009055587 A1 | 4/2009 |
| WO | WO-2009/094554 | 7/2009 |
| WO | WO-2010/058292 | 5/2010 |
| WO | WO-2010/082135 | 7/2010 |
| WO | WO-2010/119340 | 10/2010 |
| WO | WO-2010/143072 | 12/2010 |
| WO | WO-2011/013001 | 2/2011 |
| WO | WO-2011/024074 | 3/2011 |

OTHER PUBLICATIONS

Clement et al., "Enhanced ultrasound transmission through the human skull using shear mode conversion" J. Acoust. Soc. Am. 115 (3), Mar. 2004, pp. 1356-1364.*

McGough et al., "Direct Computation of Ultrasound Phased-Array Driving Signals from a Specified Temperature Distribution for Hyperthermia," IEEE Transactions on Biomedical Engineering, vol. 39, No. 8, pp. 825-835 (Aug. 1992).

Botros et al., "A hybrid computational model for ultrasound phased-array heating in presence of strongly scattering obstacles," IEEE Trans. on Biomed. Eng., vol. 44, No. 11, pp. 1039-1050 (Nov. 1997).

Cain et al., "Concentric-ring and Sector-vortex Phased-array Applicators for Ultrasound Hperthermia," IEEE Trans. on Microwave Theory & Techniques, vol. MTT-34, No. 5, pp. 542-551 (May 1986).

Chen et al., "MR Acoustic Radiation Force Imaging: Comparison of Encoding Gradients.", (2008).

Cline et al., "Focused US system for MR imaging-guide tumor ablation," Radiology, v. 194, No. 3, pp. 731-738 (Mar. 1995).

Cline et al., "MR Temperature mapping of focused ultrasound surgery," Magnetic Resonance in Medicine, vol. 32, No. 6, pp. 628-636 (1994).

Cline et al., "Simultaneous magnetic resonance phase and magnitude temperature maps in muscle," Magnetic Resonance in Medicine, vol. 35, No. 3, pp. 309-315 (Mar. 1996).

Daum et al., "Design and evaluation of a feedback based phased array system for ultrasound surgery," IEEE Trans. Ultrason. Ferroelec. Freq. Control, vol. 45, No. 2, pp. 431-434 (1998).

de Senneville et al., "Real-time adaptive methods for treatment of mobile organs by MRI-controlled high-intensity focussed Ultrasound," Magnetic Resonance in Medicine 57:319-330 (2007).

Fjield et al, "The Combined Concentric-ring and Sector-vortex Phased Array for MRI Guided Ultrasound Surgery," IEEE Trans. on Ultrasonics, Ferroelectrics and Freq. Cont., vol. 44, No. 5, pp. 1157-1167 (Sep. 1997).

Herbert et al., "Energy-based adaptive focusing of waves: application to ultrasonic transcranial therapy," 8th Intl. Symp. on Therapeutic Ultrasound, (2009).

(56) References Cited

OTHER PUBLICATIONS

Huber et al., "A New Noninvasive Approach in Breast Cancer Therapy Using Magnetic Resonance Imaging-Guided Focussed Ultrasound Surgery," Cancer Research 61, 8441-8447 (Dec. 2001).
International Preliminary Report on Patentability in International Patent Application No. PCT/IB2004/001512, mailed Dec. 8, 2005.
International Search Report and Written Opinion in International Patent Application No. PCT/IB2004/001498, dated Aug. 31, 2004.
International Search Report and Written Opinion in International Patent Application No. PCT/IB2005/002273, mailed Dec. 20, 2005.
International Search Report and Written Opinion in International Patent Application No. PCT/IB2005/002413, mailed Nov. 22, 2005.
International Search Report and Written Opinion in International Patent Application No. PCT/IB2006/001641, mailed Sep. 25, 2006.
International Search Report and Written Opinion in International Patent Application No. PCT/IB2006/003300, mailed Feb. 14, 2008.
International Search Report and Written Opinion in International Patent Application No. PCT/IB2007/001079, mailed Dec. 10, 2007.
International Search Report and Written Opinion in International Patent Application No. PCT/IB2007/002134, mailed Dec. 13, 2007.
International Search Report and Written Opinion in International Patent Application No. PCT/IB2007/002140, mailed Dec. 29, 2008.
International Search Report and Written Opinion in International Patent Application No. PCT/IB2008/003069, mailed Apr. 27, 2009.
Jolesz et al., "Integration of interventional MRI with computer-assisted surgery," J. Magnetic Resonance Imaging. 12:69-77 (2001).
Kohler et al., "Volumetric HIFU Ablation guided by multiplane MRI thermometry," 8th Intl. Symp. on Therapeutic Ultrasound, edited by E.S. Ebbini, U. of Minn. (Sep. 2009).
Kowalski et al., "Optimization of electromagnetic phased-arrays for hyperthermia via magnetic resonance temperature estimation," IEEE Trans. on Biomed. Eng., vol. 49, No. 11, pp. 1229-1241 (Nov. 2002).
Maxwell et al., "Noninvasive thrombolysis using pulsed ultrasound cavitation therapy—Histotripsy," Abstract, U.S. Natl. Lib. of Med., NIH, Ultrasound Med. Biol. (Oct. 23, 2009).
McDannold et al., "MRI evaluation of thermal ablation of tumors and focused ultrasounds," JMRI vol. 8, No. 1, pp. 91-100 (1998).
McDannold et al., "Magnetic resonance acoustic radiation force imaging," Med. Phys. vol. 35, No. 8, pp. 3748-3758 (Aug. 2008).
Medel et al., "Sonothrombolysis: An emerging mordality for the management of stroke," Neurosurgery, vol. 65, No. 5, pp. 979-993, (2009).
Mougenot et al., "MR monitoring of the near-field HIFU heating," 8th Intl. Symp. on Therapeutic Ultrasound, edited by E.S. Ebbini, U. of Minn. (Sep. 2009).
Partial International Search Report and Written Opinion in International Patent Application No. PCT/IB2007/001079, dated Sep. 25, 2007.
Vimeux et al., "Real-time control of focused ultrasound heating based on rapid MR thermometry," Investig. Radiology, vol. 43, No. 3, pp. 190-193, (1999).
Vykhodtseva et al., "MRI detection of the thermal effects of focused ultrasound on the brain," Ultrasound in Med. & Biol., vol. 26, No. 5, pp. 871-880 (2000).
Written Opinion in International Patent Application No. PCT/IL01/00340, mailed Feb. 24, 2003.
Written Opinion in International Patent Application No. PCT/IL02/00477, mailed Feb. 25, 2003.
Written Opinion in International Patent Application No. PCT/IB03/05551, mailed Sep. 10, 2004.
"How is Ablatherm treatment performed?" http://www.edap-hifu.com/eng/physicians/hifu/3c_treatment_treat-description.htm, accessed Jan. 3, 2003.
"What is HIFU? HIFU: High Intensity Focused Ultrasound," http://www.edap-hifu.com/eng/physicians/hifu2a_hifu_overview.htm, accessed Jan. 3, 2003.
"What are the physical principles?" http://www.edap-hifu.com/eng/physicians/hifu/2c_hifu_physical.htm, accessed Jan. 3, 2003.
"How does HIFU create a lesion?" http://www.edap-hifu.com/eng/physicians/hifu/2d_hifu_lesion.htm, accessed Jan. 3, 2003.
"Prostate Cancer Phase I Clinical Trials Using High Intensity Focused Ultrasound (HIFU)," Focus Surgery, http://www.focus-surgery.com/PCT%20Treatment%20with%20HIFU.htm, accessed Jan. 3, 2003.
"Abstract" Focus Surgery, http://www.focus-surgery.com/Sanghvi.htm, accessed Jan. 3, 2003.
Exablate 2000 Specification, InSightec, Ltd. (2 pages), (2002).
FDA Approves Exablate 2000 as Non-invasive surgery for Fibroids, Oct. 22, 2004.
International Search Report and Written Opinion in International Patent Application No. PCT/IB2010/000189, mailed Jun. 1, 2010.
International Search Report for PCT/IB03/05551 completion date Mar. 2, 2004 (5 pages).
International Search Report and Written Opinion in Internation Patent Application No. PCT/IB2010/000971, mailed Jul. 29, 2010 (9 pages).

\* cited by examiner

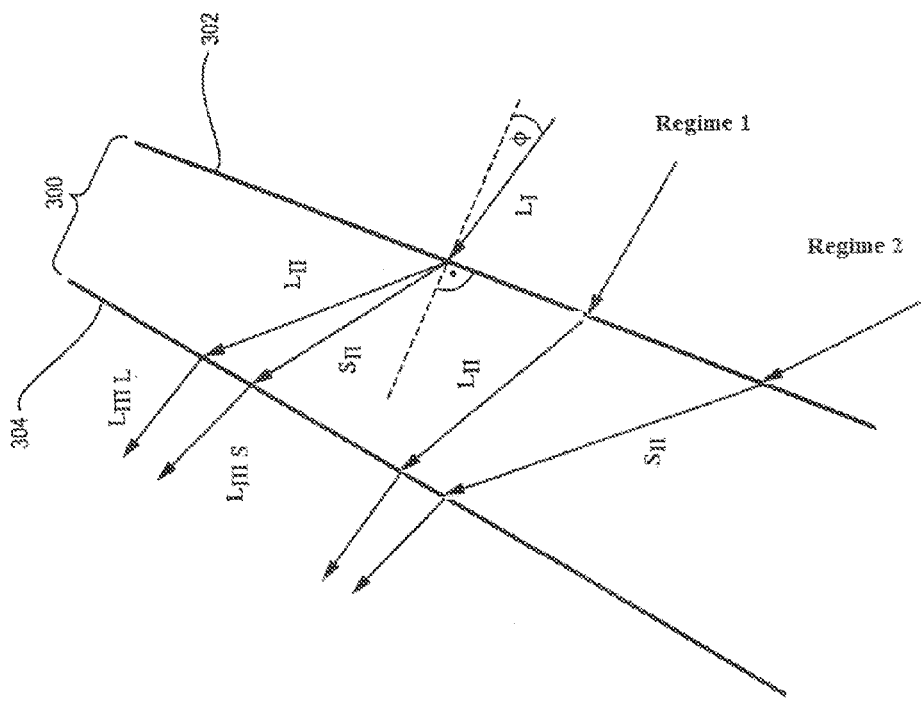
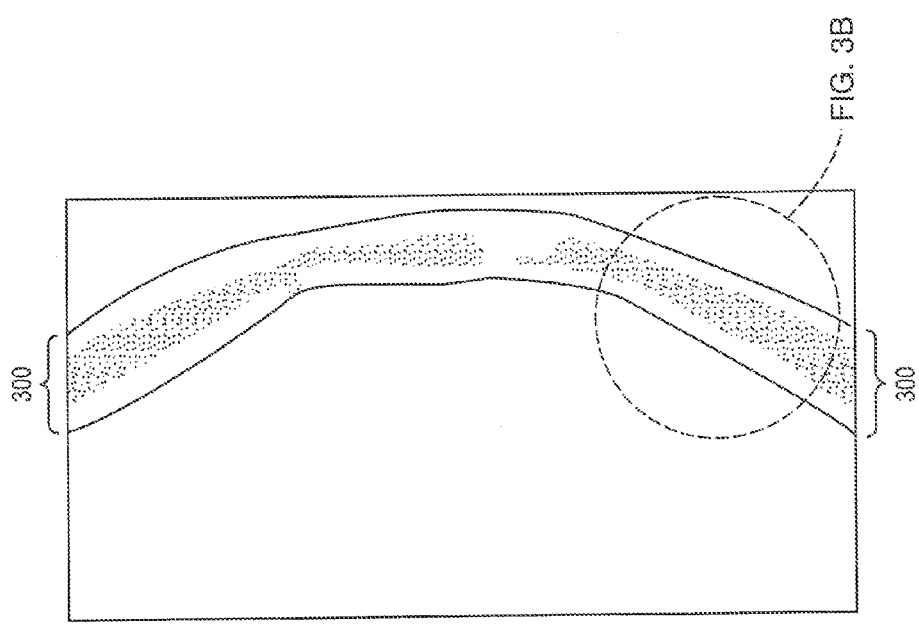

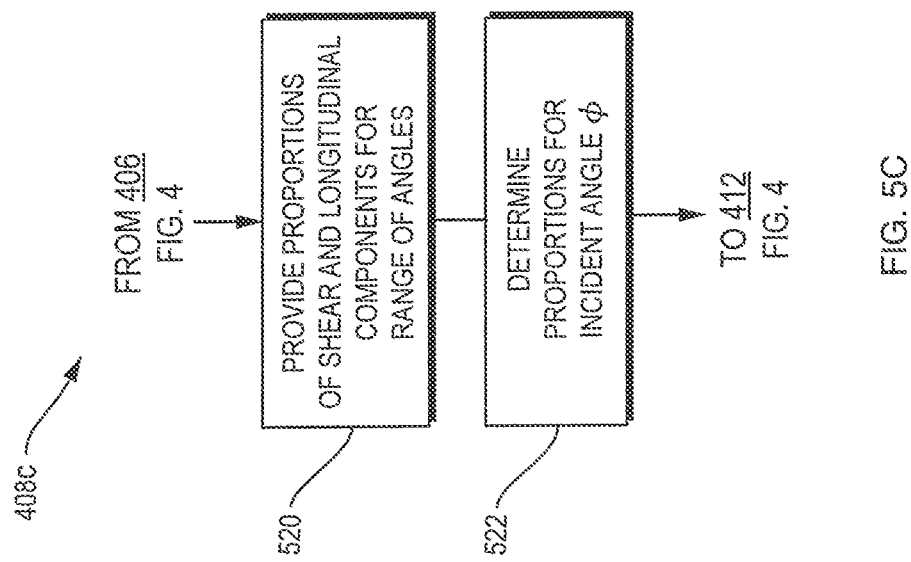

FOCUSING ULTRASOUND INTO THE BRAIN THROUGH THE SKULL BY UTILIZING BOTH LONGITUDINAL AND SHEAR WAVES

BACKGROUND

Ultrasound penetrates well through soft tissues and, due to its short wavelengths, can be focused to spots with dimensions of a few millimeters. As a consequence of these properties, ultrasound can and has been used for a variety of diagnostic and therapeutic medical purposes, including ultrasound imaging and non-invasive surgery of many parts of the body. For example, by heating diseased (e.g., cancerous) tissue using ultrasound, it is often possible to ablate the diseased portions without causing significant damage to surrounding healthy tissue.

The noninvasive nature of ultrasound surgery is particularly appealing for the treatment of brain tumors. Moreover, coherent, non-invasive focusing of ultrasound through the human skull has been considered as a tool for targeted drug delivery to the brain, improved thrombolytic stroke treatment, blood flow imaging, the detection of internal bleeding, and tomographic brain imaging. However, the human skull has been a barrier to the clinical realization of many of these applications. Impediments to transcranial procedures include strong attenuation and the distortions caused by irregularities in the skull's shape, density, and sound speed, which contribute toward destroying the ultrasound focus and/or decreasing the ability to spatially register received diagnostic information.

Several minimally invasive or noninvasive aberration-correction techniques for transskull focusing overcome the focusing difficulties at least partially. Minimally invasive approaches may use receiving probes designed for catheter insertion into the brain to measure the amplitude and phase distortion caused by the skull, and then correct the ultrasound beam using an array of transducers. An alternative, completely noninvasive approach uses X-ray computed tomography (CT) images, rather than receiving probes, to predict the wave distortion caused by the skull.

Noninvasive focusing with a therapeutic array has been demonstrated at frequencies of about 2 MHz with a longitudinal wave propagation model. The velocity of these waves is approximately 2700 m/s in the skull, and about 1500 m/s in water and soft tissue. Due to this ratio, sound that arrives at the skull under an incident angle above about 30°, the critical angle, is reflected. The amplitude of the focus therefore drops when the focus is directed close to the skull surface. As shown in FIGS. 1A and 1B, a treatment envelope 100 is defined as the region accessible to ultrasound from a sufficient number of transducers 102 to enable treatment. Whereas the effect of reflection is minimal when the target area is deep within the brain (FIG. 1A), since it lies inside the treatment envelope 100, reflection becomes problematic when the target is outside the envelope 100 (FIG. 1B). In the latter case, only a small number of transducers can reach the target area without reflection, and the closer the target is to the skull, the more transducers will be completely excluded from treatment due to reflection.

The treatment envelope 100 can be extended by reducing the frequency, e.g., to 0.2 MHz, and employing shear waves. Shear waves are largely absorbed in the skull at frequencies between 0.5 MHz and 4 MHz; at lower frequencies, however, their absorption is reduced to about that of longitudinal modes. Moreover, at 0.2 MHz, the sound velocity of shear waves in water (~1500 m/s) is comparable to that in the skull (~1400 m/s), thereby essentially eliminating the problem of reflection above a critical angle.

Previous methods of utilizing shear waves have calculated the phase shifts and amplitude attenuation associated with an originally longitudinal mode that is converted to a shear mode upon encountering the skull, and converted back to a longitudinal mode when entering the soft tissue of the brain. This approach is limited to large incidence angles at which no longitudinal mode is excited in the skull, or is otherwise inaccurate. In order to optimize focusing properties and maximize the amount of energy available in the focus, the coexistence of longitudinal and transverse modes ought to be taken into consideration.

SUMMARY

The present invention provides, in various embodiments, methods and apparatus for ultrasound focusing utilizing both longitudinal and shear modes. While developed mostly for non-invasive brain surgery and imaging, the approach of the invention may also be applied to other parts of the body requiring the penetration of ultrasound through a bone or cartilage interface. In transcranial applications, a transducer array emits longitudinal sound waves, which split into longitudinal and transverse components when entering the skull. The ratio of these two components depends on the frequency and the incidence angle. At the interface of the skull with the soft brain tissue, the transverse wave, or shear wave, is converted back to a longitudinal wave, or pressure wave, and both longitudinal components contribute to the ultrasound focus in the brain. Methods embodying the invention compute and correct for a phase shift and/or amplitude attenuation experienced by the waves during their propagation through the skull and brain.

In a first aspect, the invention provides, in various embodiments, a method for delivering ultrasound waves to a target through at least one tissue layer, which defines a first and a second interface. The waves have both a shear component and a longitudinal component through the first tissue layer. The method involves weighting energy contributions from the shear component and the longitudinal component based on an incident angle of the waves at the first interface and, optionally, further based on a frequency of the waves and/or on an acoustic response of the first layer. The method may also include the computation of a coefficient for the reflection of the waves at the first interface of the first tissue layer. Furthermore, the method includes the steps of computing phase shifts, and optionally attenuation coefficients, associated with the shear component and the longitudinal component, and compensating for the phase shifts and/or attenuations based on the weightings when delivering the ultrasound waves. The compensation step may, in some embodiments, also account for the geometry, thickness, density, and/or acoustic response of the first tissue layer. This first tissue layer corresponds in certain embodiments to a patient's skull. The method may involve providing a model of the first tissue layer (and any additional tissue layers), on which the compensation step may be based. Such a model may be obtained using computer tomography or magnetic resonance imaging. In certain embodiments, the model contains locally parallel layers.

In some embodiments, the weighting of energy contributions from the shear and longitudinal components is accomplished by determining a threshold angle, and setting the contribution from the shear component to zero for incident angles below the threshold angle and the contribution from the longitudinal component to zero for incident angles above or at the threshold angle. Alternatively, two threshold angles may be determined. In these alternative embodiments, the contribution from the shear mode is set to zero for incident angles below the smaller of the two threshold angles, and the contribution of the longitudinal mode is set to zero for angles above the larger of the two threshold angles. For incident angles between the threshold angles, the energy contributions of the two modes are computed by (e.g., linear) interpolation. In some embodiments, the weighting step is based on a relationship between energy contributions from the shear component and the longitudinal component that has been determined empirically over a range of incidence angles.

In certain embodiments, the ultrasonic wave incident upon the first interface is purely longitudinal, and excites a longitudinal and a shear component in the first tissue layer. The shear component, in turn, may excite a longitudinal wave at the second interface.

In various embodiments, the ultrasound waves are delivered by a phased array of transducers, whose outputs are adjusted according to the computed phase shifts and, if applicable, attenuations in the compensation step. The waves may have a frequency in the range from 100 kHz to 400 kHz.

In a second aspect, the invention provides, in various embodiments, a system for delivering multimode ultrasound waves to a target located inside an object that contains at least a first tissue layer defining a first and a second interface. The system includes a phased array of transducers arranged around the object, a controller computing phase shift compensations for the transducers, and a beam former in communication with the phased array of transducers for adjusting outputs of the transducers in accordance with the phase shift compensations computed by the controller. The controller receives data about the object and its location relative to the transducers, as well as about the location of the target, and uses this data to compute an incident angle at which waves emanating from the transducer arrive at the first interface. Based on the computed incidence angle, the controller computes weightings of the energy contributions from the shear component and the longitudinal component. It further calculates phase shifts for the two wave components, based on the incident angle and the data about the object, and uses these phase shifts in determining the phase shift compensations.

BRIEF DESCRIPTION OF THE DRAWINGS

The foregoing discussion and the following detailed description of embodiments of the invention can more readily be understood in conjunction with the accompanying drawings wherein:

FIG. 3A is a computer tomography image of a skull section, and FIG. 3B is a schematic diagram of an enlarged view of the skull section illustrating acoustic wave propagation through the skull;

FIGS. 5A-5C are flow charts detailing the weighting step of FIG. 4 in accordance with various embodiments of the invention;

DETAILED DESCRIPTION

Ultrasound energy may be transmitted into a patient, for various medical purposes, using arrays of radiating transducer elements. The amplitudes of the waves emanating from the elements can affect how much energy penetrates the patient, and the relative phases and amplitudes of the waves can be controlled to focus the energy into a desired region, e.g., into a tumor. While penetrating the patient, the waves typically encounter several layers of tissues, e.g., bone, muscle, or fat, whose density and structure, and, consequently, ultrasound propagation properties, differ. Due to inhomogeneities and anisotropies in the tissues, the wave fronts are often distorted. Moreover, signals from different transducer elements may encounter different thicknesses and contours of materials, and possibly air-filled or liquid-filled pockets between transducer elements and the region to be imaged or treated, resulting in different phase shifts and attenuations. Compensating for these effects, by appropriate phase shifts and amplification factors imposed on the transducer elements, avoids deterioration of focusing properties.

Figure 1B:
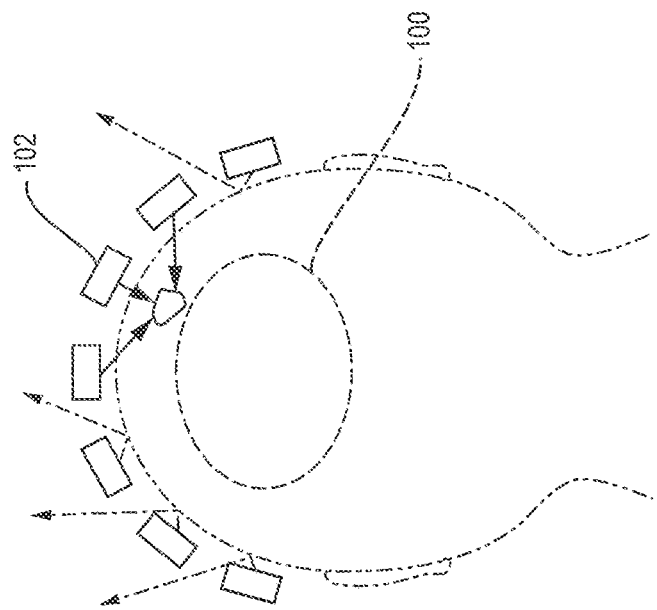
FIGS. 1A and 1B are schematic diagrams illustrating ultrasound wave focusing for foci in the center and near the periphery of the brain, respectively.
Figure 1A:
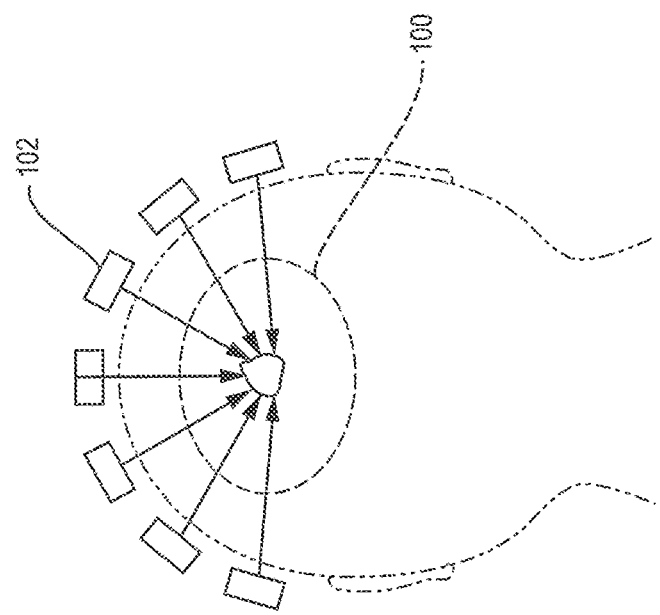
Figure 2:
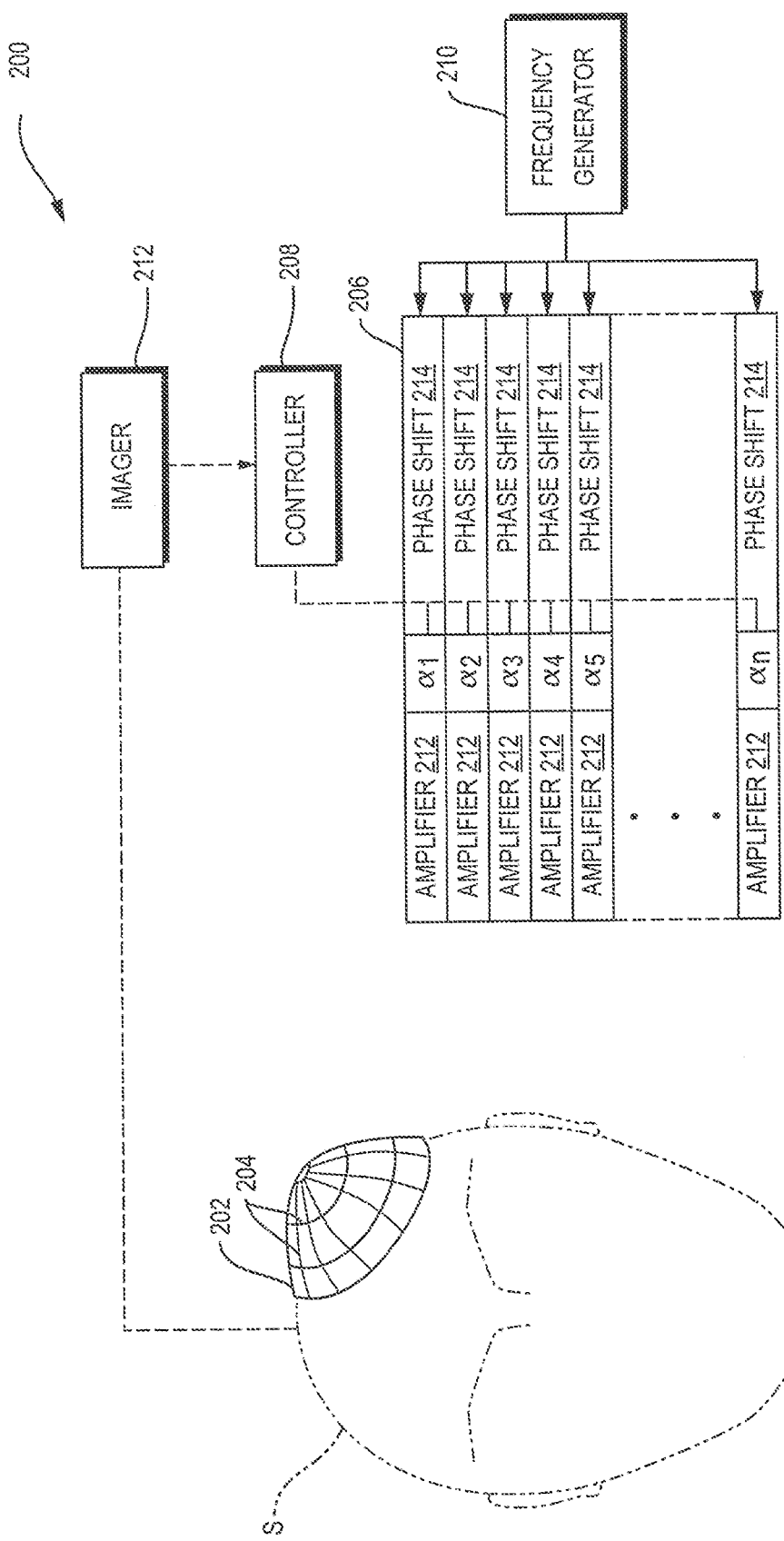
FIG. 2 is a schematic diagram of a system for focusing ultrasound in accordance with various embodiments of the invention.

FIG. 2 illustrates an exemplary ultrasound therapy system 200 for focusing ultrasound into a patient's brain through the skull S. The system 200 includes a phased array 202 of transducer elements 204, a beam former 206 driving the phased array, a controller 208 in communication with the beamformer, and a frequency generator 210 providing an input electronic signal for the beamformer. The system may further include an imager 212, such as a magnetic resonance imaging (MRI) device or a computer tomography (CT) device, for determining the structure of the patient's skull and brain.

The array 202 may comprise a single row or a matrix of transducer elements 204. In alternative embodiments, the transducer elements 204 may be arranged in a non-coordinated fashion. The array 202 may have a curved (e.g., spherical or parabolic) shape suitable for placing it on the surface of the skull S, or may include one or more planar or otherwise shaped sections. Its dimensions may vary, depending on the application, between millimeters and tens of centimeters. The transducer elements 204 of the array 202 may be piezoelectric ceramic elements, and may be mounted in silicone rubber or any other material suitable for damping the mechanical coupling between the elements 204. Piezo-composite materials, or generally any materials capable of converting electrical energy to acoustic energy, may also be used. To assure maximum power transfer to the transducer elements 204, the elements may be configured for electrical resonance at 50Ω, matching input connector impedance.

The array 202 is coupled to the beamformer 206, which drives the individual transducer elements so that they collectively produce a focused ultrasonic beam or field. For n transducer elements, the beamformer 206 may contain n pairs of an amplifier 212 and a phase delay circuit 214, each pair driving one of the transducer elements. The beamformer 206 receives a radio frequency (RF) input signal, typically in the range from 0.1 MHz to 0.4 MHz, from frequency generator 210, which may, for example, be a Model DS345 generator available from Stanford Research Systems. The input signal may be split into n channels for the n amplifiers and delay circuits 212, 214 of the beamformer 206. In some embodiments, the frequency generator 210 is integrated with the beamformer 206. The radio frequency generator 210 and the beamformer 206 are configured to drive the individual transducer elements 204 of the array 206 at the same frequency, but at different phases and different amplitudes.

The amplification or attenuation factors and the phase shift α imposed by the beamformer 206 serve to transmit and focus ultrasonic energy through the patient's skull S into a selected region of the patient's brain, and account for wave distortions induced in the skull and soft brain tissue. They are computed in the controller 208, which may provide the computational functions through software, hardware, firmware, hardwiring, or any combination thereof. For example, the controller 208 may utilize a general purpose, or special purpose, digital data processor programmed with software in a conventional manner in order to determine the phase shifts and amplification factors. In certain embodiments, the computation is based on detailed information about the structure, thickness, density, etc. of the skull. Such information may be obtained from the imager 212. Image acquisition may be three-dimensional or, alternatively, the imager 212 may provide a set of two-dimensional images suitable for constructing a three-dimensional image of the skull and brain from which thicknesses and densities can be inferred. Image-manipulation functionality may be implemented in the imager 212, in the controller 208, or in a separate device.

System 200 may be modified in many ways within the scope of the invention. For example, for diagnostic applications, the system may further include a detector device that measures transmitted or reflected ultrasound, and which may provide the signals it receives to the driver 208 for further processing. The reflection and transmission signals may also be used as feedback for the phase and amplitude adjustments of the beamformer 206. The system may contain a positioner for arresting the array 202 of transducer elements 204 with respect to the patient's skull S. In order to apply ultrasound therapy to body parts other than the brain, the transducer array 202 may take a different, e.g., a cylindrical, shape. In some embodiments, the transducer elements 204 are mounted movably and rotatably, providing mechanical degrees of freedom that can be exploited to improve focusing properties. Such movable transducers may be adjusted by conventional actuators, which may be driven by a component of controller 210 or by a separate mechanical controller.

Unlike many previous systems for focusing ultrasound through the skull, embodiments of the present invention utilize both longitudinal and shear waves. While water and soft brain tissue, for all practical purposes, only support longitudinal waves, shear waves can be excited in the much denser skull bone by longitudinal waves incident upon the skull surface. FIG. 3A shows a CT image of a skull section 300, in which the brightness level correlates with material density. The propagation of an ultrasound beam through the skull is illustrated schematically in FIG. 3B, which shows an enlarged section of the skull 300. A purely longitudinal wave $L_I$ falling onto the outer skull surface 302 splits into a shear component $S_{II}$ and a longitudinal component $L_{II}$. The relative contributions of these two components depend largely on the incidence angle. For wave frequencies between 100 kHz and 400 kHz, at angles below 20°, most of the energy of waves propagates in the longitudinal mode. At angles above 40°, the shear mode is predominant. In the intermediate regime, longitudinal and transverse modes co-exist. In general, part of the incident acoustic energy may be reflected (not shown). The remaining energy, which enters the skull, is partially absorbed, and partially propagated through the skull, depending on the frequency of the waves. For example, at frequencies above 500 kHz, most of the energy contained in the shear mode is absorbed and heats the skull. At frequencies between 100 kHz and 400 kHz, however, a significant fraction of the shear energy exits the skull at the interface 304 with the soft brain tissue, where it is transformed back into a longitudinal wave $L_{IIIS}$. The longitudinal wave $L_{II}$ likewise penetrates the bone at such frequencies, and enters into the brain tissue as a longitudinal wave $L_{IIIL}$. The two components propagate through the skull 300 under different angles due to their different propagation velocities, and, consequently, enter the brain at different locations. In order to accurately adjust the amplitudes and phases of the transducer elements to focus the acoustic energy at the desired location, the energy contributions of both components are taken into consideration.

One approach to computing the propagation of longitudinal and shear waves through the skull involves numerically solving the Navier differential equation, which fully describes acoustic wave propagation, implying both longitudinal and transverse modes. Such a numerical simulation may be carried out, for example, using the finite elements method, and is therefore amenable to an arbitrary skull structure and geometry. It facilitates optimization of the phase and amplitude adjustments of the transducer elements for a particular patient, e.g., based on a CT scan of the patient's skull. However, this method is computationally expensive, and typically is performed off-line, i.e., during treatment planning.

Various alternative approaches are based on the analysis of the propagation of individual rays. For each transducer element, the path and phase shift of an acoustic ray starting at the element, passing through the skull bone, and arriving at the focal point is calculated. Using a simplified model of the skull which contains three locally parallel (e.g., concentric spherical) layers, corresponding to two cortical layers and a marrow layer in between, a closed analytical solution for the propagation of a ray through the skull may be obtained. Similarly, the propagation through other layers, e.g., soft brain tissue layers, may be calculated. The relations between incoming and outgoing waves for the various layers may be expressed in terms of transmission matrices, the product of which yields the overall transmission matrix for propagation from the transducer element to the focus. In this method, an acoustic ray is modeled as a planar wave, and includes both longitudinal and transverse modes.

Figure 4:
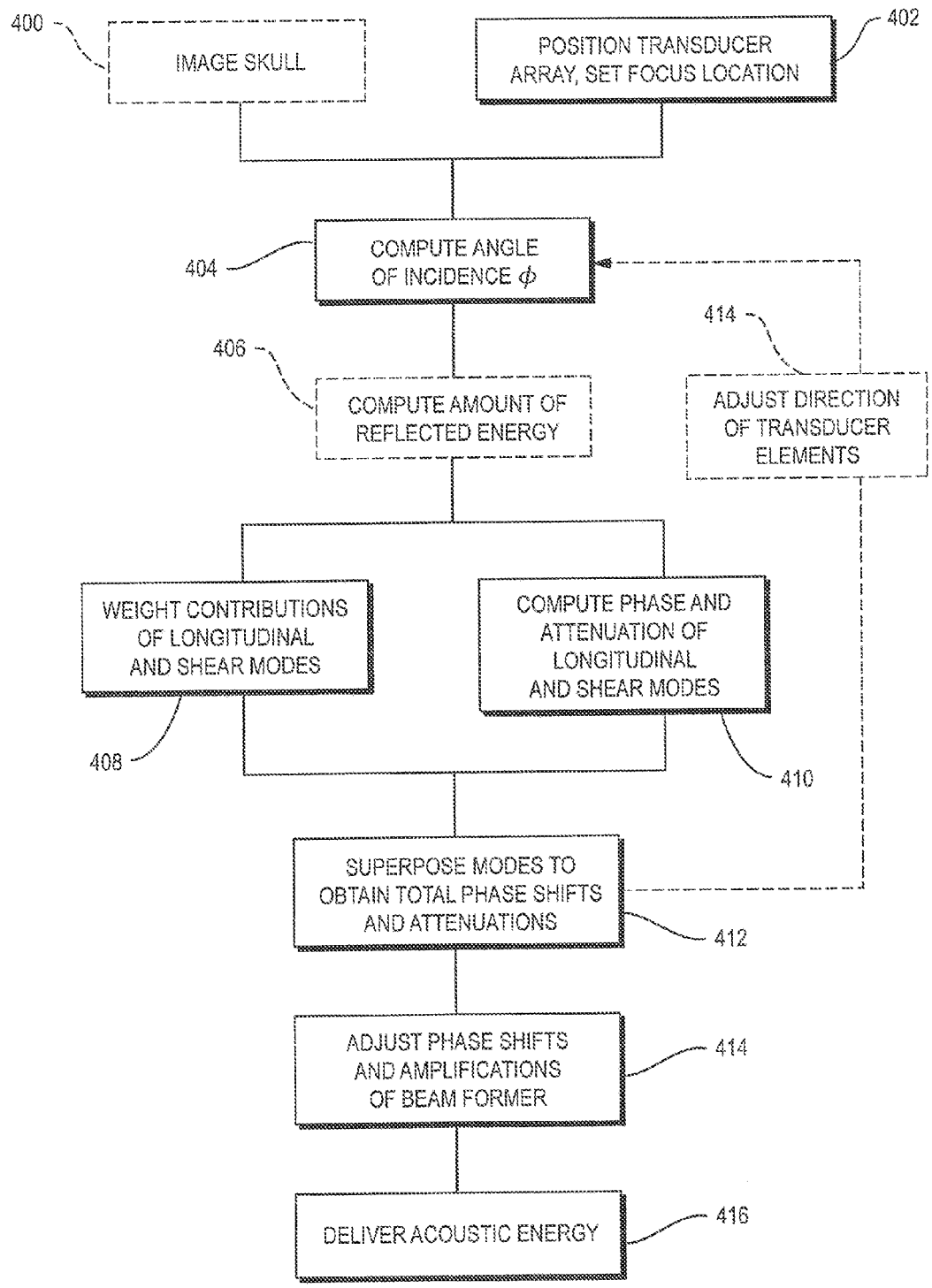
FIG. 4 is a flow chart illustrating a method for ultrasound focusing longitudinal and transverse modes in accordance with various embodiments of the invention.

A more realistic skull geometry can be accounted for in approaches that weight the contributions of longitudinal and shear modes, and calculate the propagation of these two modes separately. FIG. 4 illustrates separation methods in accordance with such approaches. In a first step 400, an image of the patient's head may be taken, e.g., by magnetic resonance imaging or computer tomography. Step 400 is optional, as an otherwise obtained model of the skull and brain may be substituted for the image. For certain applications, a simplified model, such as a series of concentric spherical layers, may suffice to focus ultrasound with adequate accuracy. In step 402, an array of transducer elements (see FIG. 2) is positioned with respect to the skull, and the desired focus of the acoustic energy is specified. The information about the skull geometry and structure and about the locations of transducer array and focus are used repeatedly throughout the following computational steps, which may be carried out by controller 208. First, an incident angle φ of the acoustic wave onto the skull is computed for each transducer element (step 404). In an optional step 406, the amount of energy reflected from the skull may be calculated based on the angle. The contributions of the transmitted energy to the longitudinal and the shear modes, respectively, are weighted in step 408, as detailed further below. In step 410, wave propagation through the skull and brain, and the phase shift and attenuation resulting at the focus, are calculated separately for each mode. Then, the contributions of the two waves are added to determine an overall phase shift and attenuation for waves emanating from the transducer element (step 412). In embodiments wherein the transducer elements can be moved or rotated, they may then be adjusted to improve the focus (step 414), and steps 404 through 412 may be repeated. Once the total phase and/or attenuation are determined for each transducer element, they are employed, in step 416, to adjust the phase shifts α and amplification factors in the beamformer. Finally, the transducer array is driven accordingly to deliver acoustic energy to the desired focus (step 418).

Figure 5B:
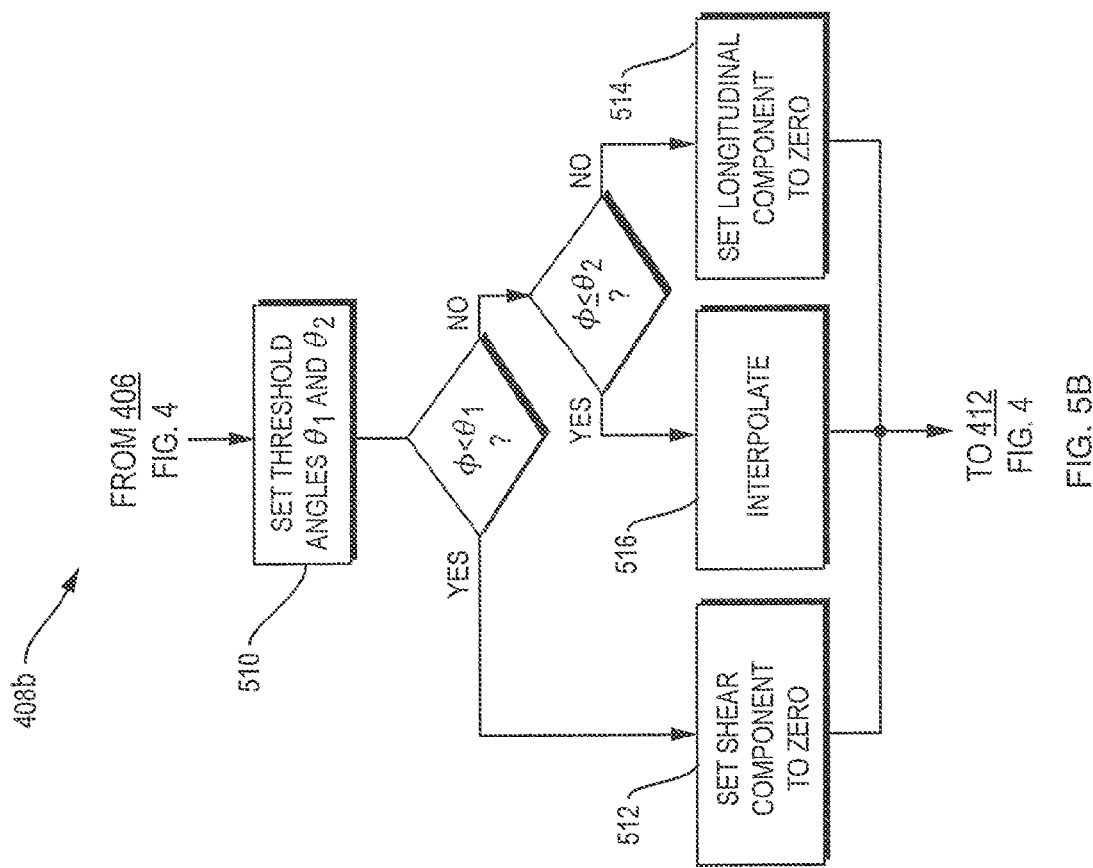
Figure 5A:
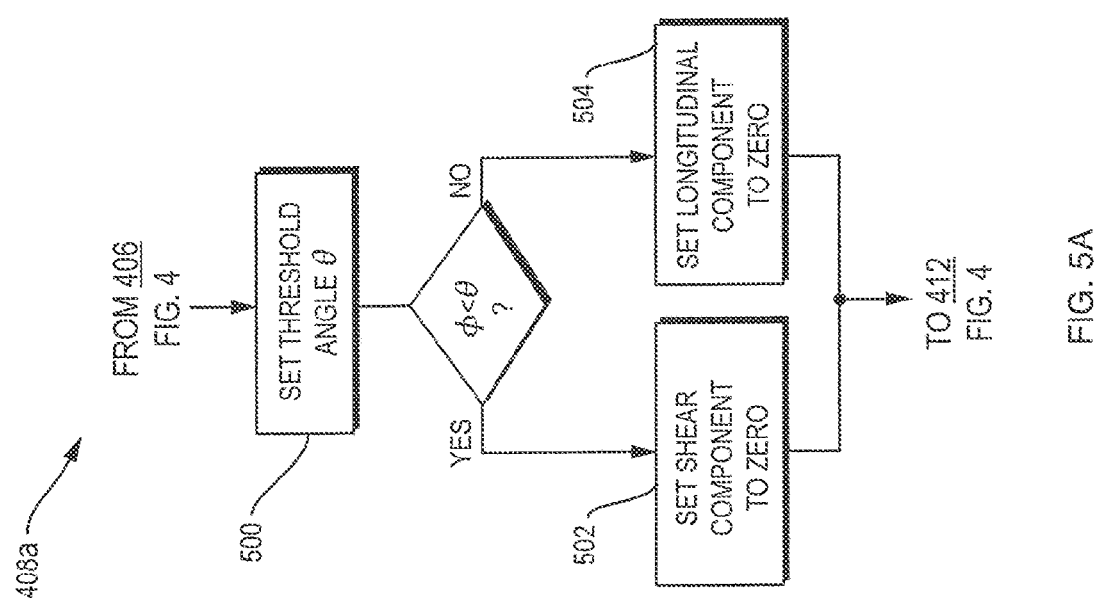

The weighting step 408 may be carried out in one of several ways of various levels of sophistication. FIGS. 5A-5C illustrate three exemplary methods. In approach 408*a*, shown in FIG. 5A, a threshold angle θ is determined (step 500), and this angle separates a predominantly longitudinal regime from a predominantly transverse regime. The threshold angle may be chosen dependent on the frequency of the waves. For example, for acoustic waves at a frequency of around 0.2 MHz, a suitable threshold angle is 30°. The energy is assumed to be carried entirely by the longitudinal mode for incidence angles below the threshold angle, and entirely by the transverse mode for incidence angles above the threshold angle. Accordingly, the energy contribution of the shear wave is set to zero below the threshold angle (step 502), and the energy contribution of the longitudinal pressure wave is set to zero above the threshold angle (step 504).

Figure 6:
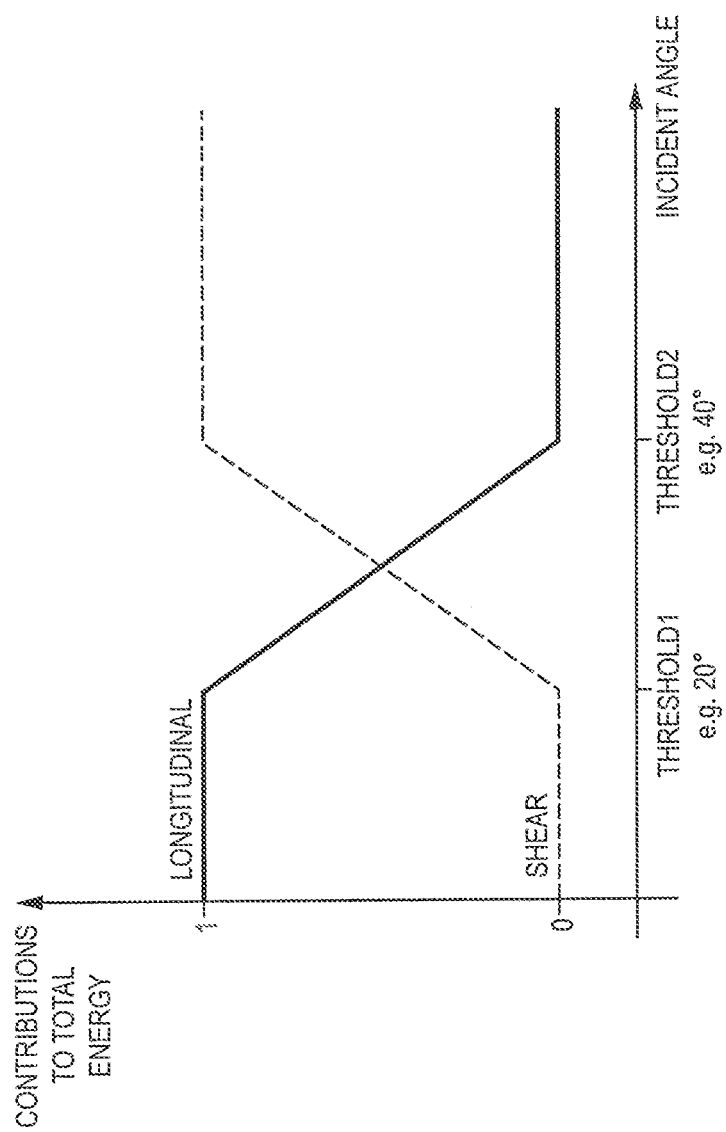
FIG. 6 is a graph illustrating an interpolation for the energy distribution between longitudinal and transverse waves in accordance with one embodiment of the invention.

FIG. 5B illustrates a more involved method 408*b*, involving three regimes—a longitudinal regime, a shear regime, and an overlap regime. In step 510, two threshold angles, $\theta_1$ and $\theta_2$, are defined. For incidence angles φ below the first, smaller threshold angle $\theta_1$, the shear component is set to zero (step 512), and for incidence angles above the second, larger threshold angle $\theta_2$, the longitudinal component is set to zero (step 514). At incidence angles between the first and second threshold angles, longitudinal and shear are assumed to coincide, and their relative contributions are determined by interpolation (step 516). For example, the fraction of the shear component may be set to increase linearly from zero percent at the first threshold angle, $\theta_1$, to one hundred percent at the second threshold angle, $\theta_2$, as illustrated in the diagram of FIG. 6. However, non-linear interpolations may also be used.

Figure 7:
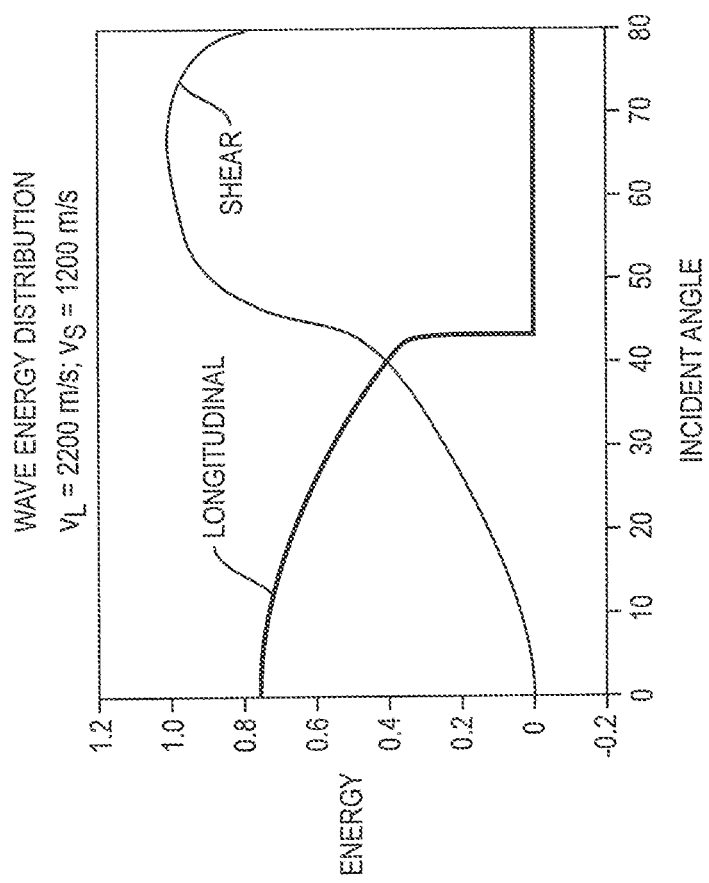
FIG. 7 is a graph showing empirical data for the energy distribution between longitudinal and transverse waves which may be used in accordance with one embodiment of the invention.

In some embodiments, illustrated in FIG. 5C, the proportions of longitudinal and shear modes are determined empirically. Such methods 408*c* involve providing, in step 520, values for the contributions of both modes over a range of incident angles, e.g., in the form of a graph. FIG. 7 is an exemplary graph showing the fraction of the incident energy that propagates through the skull in the longitudinal and transverse modes, based on empirically gathered data. At about 40°, the energy of the longitudinal mode drops to zero. The energy of the transverse mode increases from zero at normal incidence to as significant fraction at about 40°, above which angle of incidence it predominates. In step 522, weighting factors for the longitudinal and the transverse component are determined for a particular incident angle based on, for example, the relationships shown in FIG. 7.

With renewed reference to FIG. 2, steps 404-412 are typically implemented by a suitable programmable processor and computer memory. The processor may be implemented in hardware or software, or a combination of both, within controller 208 or, alternatively, in a separate device such as a general-purpose computer. In addition, the operating program of system 200 may set aside portions of a computer's random access memory to provide control logic that effects one or more of the image capture, processing, and delivery of acoustic energy via transducer array 204. In such an embodiment, the program may be written in any one of a number of high-level languages, such as FORTRAN, PASCAL, C, C++, C#, Java, Tcl, or BASIC. Further, the program can be written in a script, macro, or functionality embedded in commercially available software, such as EXCEL or VISUAL BASIC. Additionally, the software can be implemented in an assembly language directed to a microprocessor resident on a computer. For example, the software can be implemented in Intel 80x86 assembly language if it is configured to run on an IBM PC or PC clone. The software may be embedded on an article of manufacture including, but not limited to, "computer-readable program means" such as a floppy disk, a hard disk, an optical disk, a magnetic tape, a PROM, an EPROM, or CD-ROM.

Although the present invention has been described with reference to specific details, it is not intended that such details should be regarded as limitations upon the scope of the invention, except as and to the extent that they are included in the accompanying claims.

What is claimed is:

1. A method of delivering multimode ultrasound waves to a target through at least one tissue layer defining a first interface and a second interface, the waves having a shear component and a longitudinal component through the at least one tissue layer, the method comprising the steps of:

using a processor, assigning the waves to one of at least two regimes based at least in part on an incident angle of the waves at the first interface, the first regime corresponding to an incident angle smaller than a first threshold angle and the second regime corresponding to an incident angle equal to or greater than a second threshold angle;

using the processor, assigning weighting factors to the longitudinal and shear components of the waves based on the regimes to which the waves are assigned, the weighting factor of the shear component of a wave having a value of zero if the wave is assigned to the first regime and the weighting factor of the longitudinal component of a wave having a value of zero if the wave is assigned to the second regime;

using the processor, computing phase shifts associated with the shear component and the longitudinal component;

based on the weighting factors and the phase shifts, computing, using the processor, a weighted sum of the longitudinal and shear components so as to determine a total phase shift; and compensating for the total phase shift-when delivering the ultrasound waves.

2. The method of claim 1 wherein the ultrasound waves are delivered by a phased array of transducers, the compensation step comprising adjusting outputs of the transducers in accordance with the total phase shifts determined from the weighted sums of the longitudinal and shear components associated with respective transducers.

3. The method of claim 1 further comprising computing coefficients of attenuation associated with the longitudinal component and the shear component, and compensating for the attenuation when delivering the ultrasound waves.

4. The method of claim 1 further comprising computing a coefficient of reflection of the wave at the first interface, and compensating for the reflection when delivering the ultrasound waves.

5. The method of claim 1 wherein assigning the waves to the regimes is further based on a frequency of the ultrasound waves.

6. The method of claim 1 wherein assigning the waves to the regimes is further based on an acoustic response of the first layer.

7. The method of claim 1 wherein the phase shifts associated with the shear component and the longitudinal component are computed based on at least one of a geometry, a thickness, a density, and an acoustic response of the first layer.

8. The method of claim 1 wherein the at least one tissue layer corresponds to a skull.

9. The method of claim 1 wherein the first threshold angle is equal to the second threshold angle.

10. The method of claim 1 wherein the waves are assigned to the first regime, the second regime or a third regime corresponding to an incident angle equal to or greater than the first threshold angle and smaller than the second threshold angle, and wherein determining weighting factors of the shear and longitudinal components comprises, if the waves are assigned to the third regime, interpolating between respective weighting factors for the first and second regimes.

11. The method of claim 10 wherein the interpolation is linear.

12. A method of delivering multimode ultrasound waves to a target through at least one tissue layer defining a first interface and a second interface, the waves having a shear component and a longitudinal component through the at least one tissue layer, the method comprising:
    using a processor, computing phase shifts associated with the longitudinal and shear components;
    based on an empirically determined relationship between relative energy contributions from the shear component and the longitudinal component and an incident angle of the waves at the first surface, assigning, using the processor, weighting factors to the longitudinal and shear components;
    based on the weighting factors and the phase shifts, computing, using the processor, a weighted sum of the longitudinal and shear components so as to determine a total phase shift; and
    compensating for the total phase when delivering the ultrasound waves.

13. The method of claim 1 further comprising providing a model of the at least one tissue layer, and basing the phase shift computation on the model.

14. The method of claim 13 wherein the model comprises locally parallel layers.

15. The method of claim 13 wherein the model is obtained using at least one of computer tomography or magnetic resonance imaging.

16. The method of claim 1 wherein the ultrasound waves have a frequency in the range from 100 kHz to 400 kHz.

17. The method of claim 1 wherein the ultrasound wave incident at the first interface is purely longitudinal.

18. The method of claim 17 wherein the ultrasound wave incident at the first interface excites a longitudinal component and a shear component thereat.

19. The method of claim 18 wherein the shear component excites a longitudinal wave at the second interface.

20. A system for delivering multimode ultrasound waves to a target located inside an object that comprises at least a first layer defining a first interface and a second interface, the waves having a shear component and a longitudinal component through at least the first layer, the system comprising:
    (a) a phased array of transducers arranged around the object;
    (b) a controller for
        (i) receiving data about the object, its location relative to the transducers, and a location of the target,
        (ii) computing for each transducer, based on the data, (1) an incident angle at which waves emanating from the transducer arrive at the first interface, and (2) phase shifts of the shear component and the longitudinal component,
        (iii) for each transducer, computationally assigning the waves to one of at least two regimes based at least in part on the incidence angle, the first regime corresponding to an incident angle smaller than a first threshold angle and the second regime corresponding to an incident angle equal to or greater than a second threshold angle, and assigning weighting factors to the longitudinal and shear components based on the regimes to which the waves are assigned,
    the weighting factor of the shear component of a wave having a value of zero if the wave is assigned to the first regime and the weighting factor of the longitudinal component of a wave having a value of zero if the wave is assigned to the second regime; and
        (iv) based on the weighting factors and the phase shifts, computing a weighted sum of the longitudinal and shear components so as to determine a total phase shift for each transducer; and
    (c) a beam former in communication with the controller and the phased array of transducers for adjusting outputs of the transducers to compensate for the total phase shift computed by the controller.

21. The system of claim 20 wherein the first threshold angle is equal to the second threshold angle.

22. The system of claim 20 wherein the at least two regimes comprise a third regime corresponding to an incident angle equal to or greater than the first threshold angle and smaller than the second threshold angle, and wherein the controller is configured to assign waves to the first regime, the second regime or the third regime based on the incident angles of the waves and to determine weighting factors of the shear and longitudinal components of waves assigned to the third regime by interpolating between respective weighting factors for the first and second regimes.

23. A system for delivering multimode ultrasound waves to a target located inside an object that comprises at least a first layer defining a first interface and a second interface, the waves having a shear component and a longitudinal component through at least the first layer, the system comprising:
    (a) a phased array of transducers arranged around the object;
    (b) a controller for
        (i) receiving data about the object, its location relative to the transducers, and a location of the target,
        (ii) computing for each transducer, based on the data, (1) an incident angle at which waves emanating from the transducer arrive at the first interface, and (2) phase shifts of the shear component and the longitudinal component,
        (iii) for each transducer, computationally assigning weighting factors to the longitudinal and shear components based on an empirically determined relationship between relative energy contributions from the shear component and the longitudinal component and the incident angle of the waves at the first surface; and
        (iv) based on the weighting factors and the phase shifts, computing a weighted sum of the longitudinal and shear components so as to determine a total phase shift for each transducer; and
    (c) a beam former in communication with the controller and the phased array of transducers for adjusting outputs of the transducers to compensate for the total phase shift computed by the controller.

* * * * *